United States Patent [19]

Baskys et al.

[11] Patent Number: 5,494,580
[45] Date of Patent: Feb. 27, 1996

[54] METHOD OF DECONTAMINATION OF A HYDROCARBON-POLLUTED ENVIRONMENT BY THE USE OF BACTERIAL COMPOSITIONS

[75] Inventors: Egidijus V. Baskys; Saulius Grigiskis; Kestutis Vilutis, all of Vilnius, U.S.S.R.

[73] Assignee: Baltic General Investment Corporation, Barcelona, Spain

[21] Appl. No.: 129,855

[22] Filed: Mar. 30, 1993

[51] Int. Cl.$^6$ .................................................. C02F 3/34
[52] U.S. Cl. .................. 210/611; 210/909; 210/922; 435/281; 435/823; 435/831; 435/874
[58] Field of Search .................................. 210/610, 611, 210/912, 922, 908, 909; 435/262.5, 281, 831, 823, 874–877

[56] References Cited

U.S. PATENT DOCUMENTS

| | | | |
|---|---|---|---|
| 5,100,455 | 3/1992 | Pinckard et al. | 71/9 |
| 5,242,593 | 9/1993 | Oberkofler et al. | 210/611 |
| 5,314,619 | 5/1994 | Runyon | 210/610 |

Primary Examiner—Thomas Wyse
Attorney, Agent, or Firm—Flynn, Thiel, Boutell & Tanis

[57] ABSTRACT

Method of decontamination of a hydrocarbon-polluted environment by the use of bacterial compositions. The method is a process of biological decomposition of the hydrocarbons using, as decontaminating active ingredients, bacterial compositions composed of one or more strains from among the following microorganisms: *Azotobacter vinelandii* 21, Pseudomonas sp.9, Pseudomonas sp.19, Pseudomonas sp.31 and *Acinetobacter calcoaceticus* 23. In the method, prior analysis of the chemical composition of the pollutants is essential in order to select, in accordance with this composition, the mixture of strains of the most active microorganisms from among the five mentioned above, taking into account the natural conditions of the polluted environment. The bacterial composition also contains inorganic salts supplying N and P, and additives needed for bacterial growth.

The method is used to decontaminate hydrocarbon-polluted soils, fresh water, salt water, waters from technological processes and industrial waste waters or effluents.

17 Claims, 5 Drawing Sheets

METHOD OF DECONTAMINATION OF A HYDROCARBON-POLLUTED ENVIRONMENT BY THE USE OF BACTERIAL COMPOSITIONS

FIELD OF THE INVENTION

The present invention relates to the protection of the environment, methods and products being provided for the effective decontamination of soils, waters and other industrial effluents polluted with petroleum or petroliferous derivatives.

BACKGROUND OF THE INVENTION

Extraction of petroleum on land or in the sea, its transport by sea or overland and its transfer and handling in refineries and on loading and discharging frequently give rise to an appreciable deterioration of the environment caused by leakages or accidents, pollution of marine or terrestrial regions being caused sporadically or continuously on account of petroleum hydrocarbons.

Various methods aimed at combating these causes of environmental contamination are known. Some methods are very basic, employing various surfactant chemical products in an effort to emulsify the petroliferous products in the water, relying on various natural bacteria which may exist in the region to degrade the hydrocarbons. However, this does not assure complete degradation, apart from which the time needed for the outcome to be reasonably acceptable can, in the best of cases, be excessively long.

Other, more truly biological methods employ various strains of microorganisms for the regeneration of marine or terrestrial regions polluted with hydrocarbons.

In EP 007,742 (1981), Pseudomonas strains are used, artificially modified so that they exhibit accelerated growth, developed in culture media to which hydrocarbons are added. However, this method is poorly effective in the decomposition of pollution with highly concentrated products, and generally requires long periods of time.

EP 0,289,350 (1988) employs *Pseudomonas putida F 1* for the decomposition of hydrocarbons, but the method is suited specifically to the decomposition of halogenated hydrocarbons, but not to petroliferous hydrocarbons.

U.S. Pat. No. 4,822,490 specifically employs *Pseudomonas putida 36*, in the form of bacterial compositions also containing inorganic salts, to degrade petroliferous pollutions. However, this method is not equally effective in combating diverse petroliferous pollutions, especially in sea water.

SUMMARY OF THE INVENTION

The present invention develops a more effective microbiological method of decontamination of soils and waters polluted with hydrocarbons, based fundamentally on the use in each case of the bacterial composition which is most effective in the decontaminating action and composed of a series of natural microorganisms, the bacterial composition being adapted in each situation to the particular circumstances of the case.

On the basis of the principle that not all bacterial strains decompose all the hydrocarbons contained in petroleum or in petroliferous products at the same rate, or with the same efficacy, some bacterial compositions composed of strains of bacteria selected specifically in accordance with the class and quantity of hydrocarbons present in the polluted region are prepared, following chemical analysis, as decontaminating agents, making the mixtures of the most effective bacteria in the same proportions in which the different types of hydrocarbons are present. Inorganic salts, especially ones supplying nitrogen and phosphorus, and other appropriate additives for achieving a more rapid growth of the selected microorganisms, are also added to the mixtures of the different bacterial preparations.

The growth of the selected microorganisms may be increased by adding protein-containing substances after acid or enzymatic hydrolysis. The waste products of food or feed industry (like corn steep liquor) or single cell protein (like yeasts grown on hydrocarbons) or waste treatment sludge can be used.

An objective of the present invention is, therefore, to develop a rapid and effective method of decontamination of soils, fresh or salt waters, ground waters, waters from technological processes or industrial effluents polluted with the hydrocarbons contained in petroleum or petroliferous products.

Another objective of the invention is to achieve the most effective decontamination by applying a bacterial composition containing the single microorganisms or mixtures of microorganisms selected from five species of bacteria of natural origin, and which is the most effective given the circumstances of the pollution involved in each case.

It is also an objective of the invention to make the selection of the microorganisms to be applied in each case by taking into account the results of the qualitative and quantitative chemical analyses carried out on the pollutant petroliferous agent. The bacterial compositions are prepared with the different species of bacteria more specifically designated, and in the appropriate proportions, for achieving the maximum and most rapid decomposition of the different hydrocarbons found on analysis. In this selection, in addition to the class of pollutant hydrocarbons, the natural conditions of the polluted region and the circumstances of each case are also taken into account.

The present invention therefore affords, in essence, the great advantage of not being limited to the application of only one particular bacterial species in any case of environmental pollution with petroliferous hydrocarbons, however well adapted that species may have been, by genetic or chemical manipulation, for combating pollutions with petroleum. The compositions of different petroleums are very different, as are the natural conditions of the polluted region, depending on whether it is soil, fresh water or salt water, more or less polluted industrial waters, and the like. The invention affords the novelty of choosing the most appropriate bacterial composition for each particular case, suitable bacterial compositions for the particular hydrocarbons and the natural conditions of each case being prepared in the appropriate proportions.

DETAILED DESCRIPTION OF THE INVENTION

Figure 1:
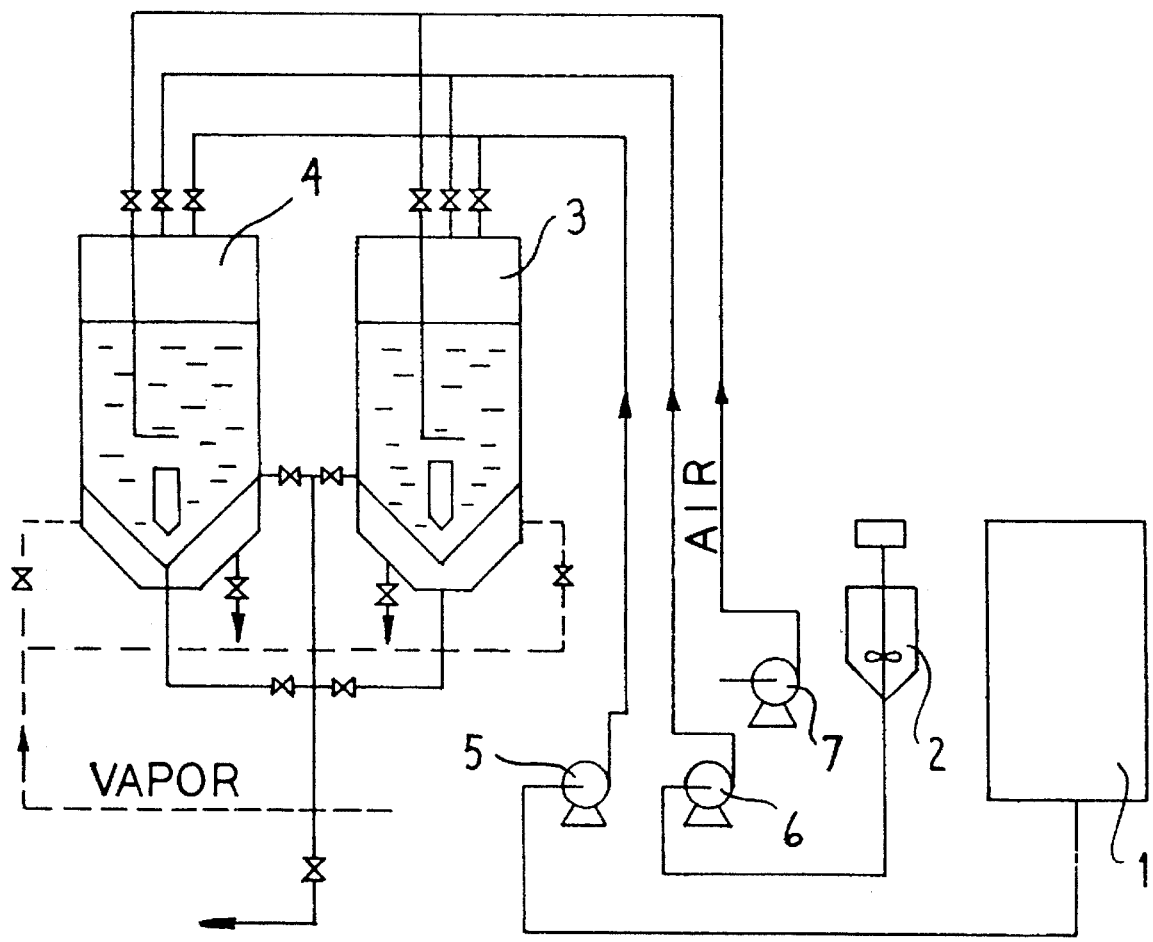
FIG. 1 illustrates a system that can be used in the present invention that utilizes two batch flow reactors with partial recirculation of the water.

According to the method of the invention, bacterial compositions are used which are composed of various strains of bacteria of natural origin, chosen from those existing in nature, which have degradative properties with respect to petroliferous products. None of the five strains chosen as the basis of the bacterial compositions to be used for decontamination has undergone any artificial genetic mutagenesis.

The bacterial species chosen for the invention are the following:

*Azotobacter vinelandii* 21 and *Acinetobacter calcoaceticus* 23, which were isolated from petroleum-polluted water near the island of Porto Santo (Portugal) in 1990.

Pseudomonas sp. 9, isolated in a petroleum-polluted fjord in Oslo, near Hotten (Norway) in 1991.

Pseudomonas sp. 19 and pseudomonas sp. 31, isolated in the petroleum-polluted bed of a railway at Vaidotai (Luthuania) station in 1989.

All these bacteria belong to the "BIOCENTRAS" microorganism collection, and have been previously characterized by their capacity to degrade various component hydrocarbons of petroleum (anthracene, octadecane, decalin, asphaltenes) specifically, taking into account the various natural conditions (soil, fresh or salt water).

The microorganisms of the invention have been deposited at the "Research Institute for Genetics and Industrial Microorganism Breeding (VNII Genetika)" in Moscow, and have the following characterizations:

*Azotobacter vinelandii* 21 . . . B-5980

Pseudomonas species 9 . . . VKPM B-6568

Pseudomonas species 19 . . . VKPM B-6569

Pseudomonas species 31 . . . VKPM B-6570

*Acinetobacter calcoaceticus* 23 . . . VKPM B-6567.

The selected microorganisms are applied for the treatment of the polluted area in the form of powder suspended in an aqueous solution of inorganic salts and additives. The class of bacteria to be used, and the quantity thereof, as well as the quantity of inorganic salts and additives needed for promoting the growth of the microorganisms, are determined in accordance with the analytical result on the pollutant and on assaying the total quantity thereof. The quantity of bacterial agent required is calculated in accordance with the relationship: 250 g of powdered bacterial preparation/ton of pollutant product.

The proportions of different species of bacteria to be used in each case should be the same as that existing between the various classes of hydrocarbons of the pollutant.

The quantity of inorganic salts supplying nitrogen and phosphorus is calculated by taking as a basis the carbon content of the total of pollutant hydrocarbons, in the proportion: $C/N/P = 100/1/0.1$ approximately.

The additives for promoting the growth of the microorganisms are added in a concentration of 0–2 g/l of bacterial suspension to be sprayed.

The aqueous suspension of the microbial preparation and inorganic salts and necessary additives is sprayed over the polluted region in the proportion of 1 liter of water per $m^2$ of polluted area.

The practical manner of preparing the bacterial compositions is: to dilute first in water the inorganic salts supplying nitrogen and phosphorus (for example, inorganic fertilizers may be used), additives needed for promoting the growth of microorganisms and the powdered bacterial preparation is then added, stirring thoroughly to obtain a good suspension. This suspension is the one sprayed over the polluted region.

The method of decontamination which is the subject of the invention, and the bacterial compositions used in this method, do not present any risk of side effects due to residual toxic metabolites. The final products of the bacterial degradation of hydrocarbons are carbon dioxide, water and bacterial cells. The first two are obviously non-toxic. The bacterial cells isolated from the natural environment have been evaluated for their toxicity on mice and rats, and are qualified as belonging to group IV of microorganisms, which is the least toxic.

The bacteria used in the present invention are non-sporeforming microorganisms, and disappear through "self-consumption" in the absence of nutrients in closed systems. In open systems (nature, for example), they come to form part of the naturally existing carbon, nitrogen and phosphorus cycles. Generally speaking, the quality of soils improves after the application of the bacteria of the invention. In aqueous systems, these microorganisms constitute nutrients for higher organisms.

The limiting step in the biodegradation process is the introduction of the first oxygen atom into the molecule of the hydrocarbon. When this step has been accomplished, intermediate products are formed, such as alcohols and fatty acids which are nutrient substances for a considerably larger number of bacterial strains naturally occurring in the environment, and which thus contribute to the decontamination.

The method of the invention has the advantage that, apart from being applied for the "in situ" decontamination of polluted regions, it can also be applied for the decontamination of soils in suitable stationary installations. In addition, appropriate stationary installations may be used for the decontamination of waters from technological processes or industrial effluents polluted witch petroliferous products, using bioreactors. In these installations, it is possible to work in continuous or discontinuous processes.

The method proposed in the invention may be used for the decontamination of hydrocarbon-polluted ground waters. In this case, the water is extracted by pumping from a well in the center of the polluted region, a mechanical cleaning of the extracted water is carried out and the latter is subsequently treated with the appropriate mixture of microorganisms in bioreactors. The regenerated water is returned to the ground, either to the various test wells made previously in order to define the affected area, or else by spraying it over the polluted ground.

It is also possible to use the method described from the regeneration, and subsequent recycling, of the polluted water in closed-circuit car wash installations.

When the method of decontamination is used in the stationary installations mentioned above for various applications, it possesses the advantage that the pH, temperature and aeration can be regulated, these parameters being maintained in each particular case at the most appropriate known levels for the development of the species of bacteria selected in each case, according to the classes of hydrocarbons present in the pollution.

Implementation of the method described in the present invention requires the following steps:

Evaluation of the activity of the isolated bacterial strains for the decomposition of different hydrocarbons.

Evaluation of the activity of the isolated bacterial strains for the decomposition of petroleum crude under different natural conditions.

Selection of the most suitable composition of microorganisms, according to the chemical composition of the pollutant and the natural conditions of the polluted region.

Production of the selected bacterial preparations.

Production of the decontaminating bacterial composition.

Application of the bacterial composition to the polluted region.

The explanation of all these steps is given below.

Evaluation of the activity of the isolated bacterial strains for the decomposition of different hydrocarbons.

The activity of the five bacterial strains mentioned above for the decomposition of various hydrocarbons which are normally components of petroleum crudes was determined by measuring the degree of decomposition (%) and the time (hours) needed to reach this degree of decomposition.

The data appear in Table 1.

TABLE 2

| | | decomposition (%) (14 days) | | |
|---|---|---|---|---|
| | | | in water | |
| No. | Microorganism | in soil | fresh | salt |
| 1 | Azotobacter vinelandii 21 | 62.0 | 87.4 | 46.8 |
| 2 | Pseudomonas sp. 9 | 65.4 | 82.5 | 68.3 |
| 3 | Pseudomonas sp. 19 | 78.1 | 53.1 | 15.8 |
| 4 | Pseudomonas sp. 31 | 62.4 | 64.0 | 24.2 |
| 5 | Acinetobacter calcoaceticus 23 | 55.2 | 60.8 | 50.5 |

From inspection of the results in Table 2, it may be concluded that, to degrade a pollution caused by a petroleum crude in different situations:

The strain Pseudomonas sp. 19 is deemed the most effective for the decontamination of soils.

The strain *Azotobacter vinelandii* 21 is deemed the most effective for the purification of fresh water polluted with petroleum crude.

The strain Pseudomonas sp. 9 is deemed the most suitable when the pollution is in salt water.

TABLE 1

| | | degree (%) and time of decomposition of hydrocarbons | | | | | | | | |
|---|---|---|---|---|---|---|---|---|---|---|
| | | | | | | | | ASPHALTENES | | |
| | | ANTHRACENE | | OCTADECANE | | DECALIN | | aromat. portion | | aliphat. portion |
| No. | Microorganism | % | hours | % | hours | % | hours | % | hours | % | hours |
| 1 | Azotobacter vinelandii 21 | 66.2 | 5.0 | 27.3 | 24.0 | 44.4 | 24.0 | 27.5 | 7.0 | 17.4 | 7.0 |
| 2 | Pseudomonas sp. 9 | 36.2 | 5.0 | 94.1 | 16.0 | 66.6 | 16.0 | 21.0 | 7.0 | 10.2 | 7.0 |
| 3 | Pseudomonas sp. 19 | 23.2 | 5.0 | 82.6 | 16.0 | 30.1 | 24.0 | 10.0 | 7.0 | 9.5 | 7.0 |
| 4 | Pseudomonas sp. 31 | 63.0 | 5.0 | 11.0 | 28.0 | 68.4 | 16.0 | 41.0 | 7.0 | 24.0 | 7.0 |
| 5 | Acinetobacter calcoaceticus 23 | 47.0 | 5.0 | 34.6 | 24.0 | 30.9 | 24.0 | 33.3 | 7.0 | 19.8 | 7.0 |

From the data in Table 1, the following are deduced:

The strain *Azotobacter Vinelandii* 21 is the most suitable one for the degradation of aromatic compounds—anthracene.

The strains Pseudomonas sp. 9 and Pseudomonas sp. 19 are the most effective ones in the degradation of aliphatic compounds—octadecane.

The strain Pseudomonas sp. 31 is the one which effects greatest degradation in naphthenic compounds—decalin.

The strain Pseudomonas sp. 31 and *Acinetobacter calcoaceticus* 23 are the ones which show greatest activity for the degradation of asphaltenes.

Evaluation of the activity of the isolated bacterial strains for the decomposition of petroleum crude under different natural conditions.

The activity of the five bacterial strains which are the subject of the invention in the degradation of a petroleum crude was determined under different natural conditions. The percentage decomposition of the crude in soil, in fresh water or in salt water was determined in a period of 14 days. The petroleum crude used contained alkanes, aromatics, naphthenes and asphaltenes. The data appear in Table 2.

Selection of the most suitable composition of microorganisms.

Combination of the results in Tables 1 and 2 make it possible to select the combination of bacterial strains which are most effective in the degradation of the hydrocarbons for each particular case of pollution with petroliferous products.

An essential ingredient for making this selection properly is to carry out a qualitative and quantitative analysis of the products causing the pollution, with the object of establishing the relationship existing between the various types of hydrocarbons. On the basis of this knowledge, the most suitable bacterial strains are preselected. If, in addition, account is taken of the physical nature of the polluted area, and the differing activity of some strains under these conditions, selection of the most appropriate species of microorganisms can then be completed, the decision being made as to which classes of bacteria, and in what proportion, should form the decontaminating bacterial composition.

By comparing the results in Table 1 with those in Table 2, it may be concluded that, although Pseudomonas sp. 9 is the best strain for decomposing alkane hydrocarbons, on the other hand it is worse at decomposing petroleum crude in soil than Pseudomonas sp. 19. Similarly, Pseudomonas sp. 31 is the best at degrading asphaltenes, but worse at degrading petroleum crude in salt water than *Acinetobacter calcoaceticus* 23.

Summarizing the data in Tables 1 and 2, the results shown in Table 3 may be obtained. These data may be used to pinpoint the selection of bacteria to be used in each particular case.

TABLE 3

| Bacterial strain | Chemical nature of the hydrocarbons | Characteristics of polluted area |
| --- | --- | --- |
| *Azotobacter vinelandii* 21 | aromatics | soil, water |
| *Pseudomonas sp.* 9 | aliphatics | water |
| *Pseudomonas sp.* 19 | aliphatics | soil |
| *Pseudomonas sp.* 31 | asphaltenes | soil, fresh water |
| *Acinetobacter calcoaceticus* 23 | asphaltenes | sea water |

By way of illustration, and as a hypothetical case of a soil polluted by a leakage of petroleum crude, the situation is as follows: Chemical analysis of the pollutant shows a content of 58.2% of aromatics, 30.8% of aliphatics and 10% of asphaltenes. Making use of Table 3, a bacterial composition should be prepared containing 6 parts of *Azotobacter vinelandii* 21, 3 parts of Pseudomonas sp. 31 and 1 part of Pseudomonas sp. 19.

Production of the bacterial preparations.

The bacterial preparations of the isolated strains which are the subject of the invention are produced by culturing the isolated microorganisms mentioned above in culture media containing 2% of starch, 3% of corn steep liquor, 0.4% of $K_2HPO_4$ and 0.25% of $KH_2PO_4$, with a pH=7.0–7.2. Culturing is carried out at 28°–30° C., with an aeration of 1 volume of air/1 volume of medium for 1 minute.

When the fermentation process has finished, the bacterial culture suspension is concentrated. If it is desired to obtain a preparation in powder form, the bacterial concentrate is mixed with protective media and dried by atomization. The powder type preparation may be stored at room temperature for 2 years.

A paste type bacterial preparation is produced by centrifuging the bacterial concentrate, mixing the bacterial biomass with protective media and freezing. The paste type preparation may be stored at −10° to −30° C. for 1 year.

Application Of the bacterial composition in the polluted region.

Once the selection of the bacterial preparations which are to form part of the decontaminating composition has been made, the preparations of bacteria are reactivated and mixed with a solution of inorganic salts supplying nitrogen and phosphorus, in an approximate proportion of 100 parts of C (in the pollutant)/10 parts of N/1 part of P. Additives needed for bacterial growth are also added. The prepared microbial suspension is aerated for 8–20 hours, and sprayed over the polluted area, or used in the stationary installations appropriate to each case.

The stationary biological treatment plants in which the decontamination processes may be carried out correspond to different types, depending on their application. Some of these are described below.

Purification plant for waters from technological processes contaminated with petroliferous products.

The unit contains 2 discontinuous type reactors, with partial recirculation of water (FIG. 1).

The scheme of operation is as follows:

The hydrocarbon-polluted water is pumped by the pump (5) from a pollutant accumulation tank (1) to the reactor (3), which fills to ⅔ of its capacity. The decontaminating bacterial composition is prepared in the reactor (2), according to the method of the invention, in accordance with the chemical analysis of the pollutant, the most appropriate strains being selected. The reactor (3) possesses steam heating and mixing systems. When the temperature of the reactor (3) reaches 30° C., the prepared bacterial composition is pumped by pump (6) from the reactor (2) to the reactor (3), where air is supplied by the compressor (7). The starting concentration of hydrocarbon-degrading bacterial cells is required to be no less than $10^6$–$10^7$ cell/ml of polluted medium. The volume of decontaminant is required to be approximately 1–5% of the polluted medium contained in reactor (3). The process of decomposition of the hydrocarbons is subjected to monitoring; after 7–10 days of treatment, part of the purified water containing microorganisms which oxidize the hydrocarbons is transferred to the reactor (4). The remaining water discharges to a sedimentation tank. The biomass of microorganisms is allowed to sediment and the supernatant layer is discharged.

The process of decontamination continues in the reactor (4), in which the polluted water accumulates. The quantity of pollutant is determined, and the inorganic salts and additives needed for growth of the microorganisms are added into the reactor (4). After the decontamination, a part of the water from the reactor (4) is returned to the reactor (3).

During the process, the concentration of microorganisms in the reactors (3) and (4) is monitored. The concentration of bacteria should be not less than $10^6$ cells/ml. If the concentration of degrading microorganisms is sufficient, the process is continued. If the bacterial concentration falls below this limit, more bacterial composition is prepared in the reactor (2).

Decontamination plant for hydrocarbon-polluted waste waters.

Methods of biological purification of hydrocarbon-polluted waste waters in continuous systems with activated sludges are well known. The drawback of these methods is their sensitivity to a limiting excessive concentration of hydrocarbons, which causes an increase in the toxicity of the water and interrupts the action of the purification system for a long period of time.

The technological variant can act in the purification of water polluted with an unlimited quantity of hydrocarbons.

Figure 2:
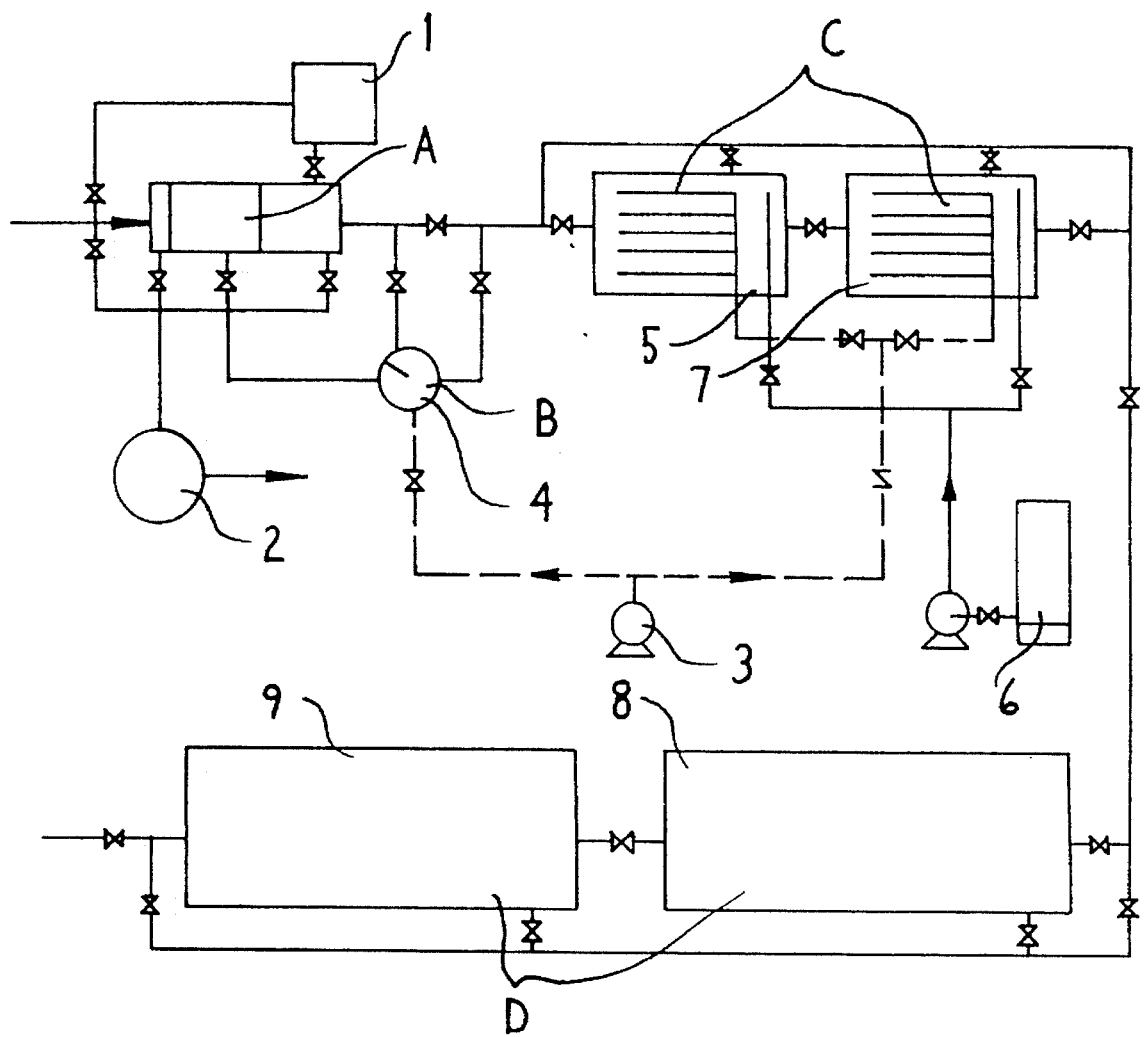
FIG. 2 illustrates a plant for treating hydrocarbon-polluted waste waters using the method of the present invention.

The biotreatment system of the invention may be carried out in the plant shown diagrammatically in FIG. 2, and consists of:

A. Three-phase mechanical cleaning unit, with partial return of pollutants and with protective device for unforeseen mild discharges of effluents.

B. Flotation unit designed for the separation of pollutant hydrocarbons from the water.

C. Two bioreactors, connected in series and in parallel. The bioreactors can work periodically and separately. They have mixing and aeration devices. When necessary, it is possible to introduce water into the bioreactors.

D. Two settlers, which can work in parallel periodically or in continuous fashion.

The system of working in this plant can be as follows: First, the polluted water is transferred to a mechanical cleaning installation (A). This installation has a reserve tank (1) for collecting accidental discharges of effluents, and a tank (2) for storing pollutants. The mechanically cleaned water is subsequently transferred to a flotation unit (4), where the hydrocarbons emulsified by the action of compressed air (compressor 3) are collected.

After flotation, or directly after mechanical cleaning, the water is drained to a biological treatment tank until ⅔ of its volume is filled.

On the basis of the methodology of the invention, the chemical contents of the petroliferous pollutants are determined, the microorganisms suitable for decomposition are selected and the quantities of inorganic salts and necessary additives are calculated. A solution of these compounds is prepared in the reactor (6). Mixing and aeration are started in the reactor (5) and the contents of the reactor (6) are transferred thereto, starting the process of biological treatment of the water. The starting concentration of hydrocarbon-degrading bacterial cells is required to be no less than $10^6$–$10^7$ cell/ml of polluted medium. The volume of decontaminant is required to be approximately 1–5% of polluted medium contained in reactor (5). In parallel with the reactor (5), the polluted water is introduced into the reactor (7) (up to ⅔ of its volume). After 4–5 days from the start of the process in the reactor (5), part of the purified water containing the microorganisms which oxidize the hydrocarbons is transferred to the reactor (6), and the remaining water is separated in a settling tank (8 or 9). The supernatant layer is subsequently separated. The biological treatment process is repeated in the first or second bioreactor. When it is estimated that there is a decrease in the effectiveness of the biological treatment, the concentration of microorganisms which degrade the hydrocarbons is determined. If the concentration is less than $10^6$ cells/ml, the composition prepared in the reactor (6) is added.

Decontamination of hydrocarbon-polluted ground waters.

Figure 3:
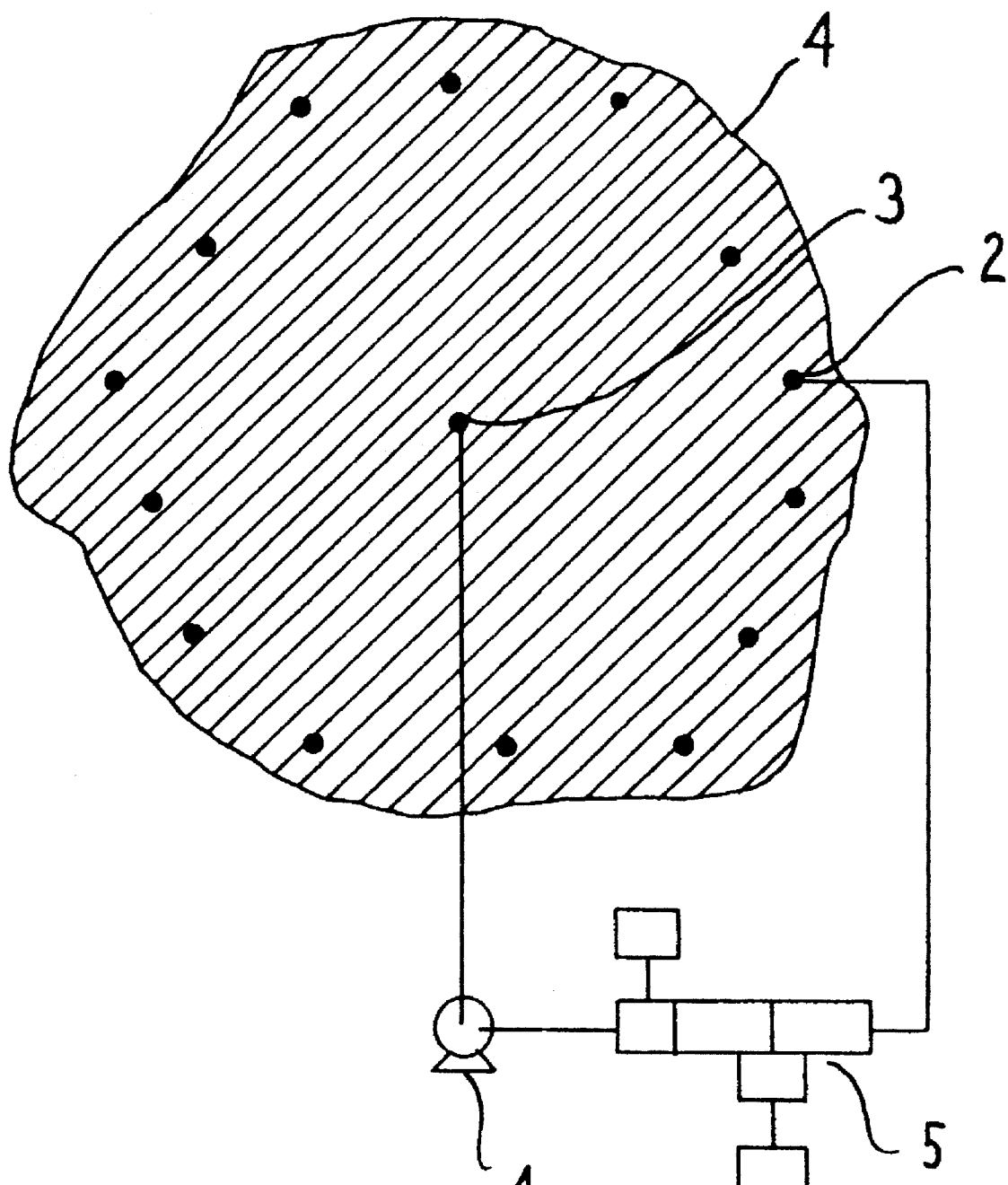
FIG. 3 illustrates a system for decontaminating hydrocarbon-polluted ground waters using the method of the present invention.

The pollutant hydrocarbons of ground waters may be decomposed, according to the invention, in accordance with the diagram in FIG. 3.

The system is as follows: Test wells (2) are bored in the polluted region to determine the extent of the polluted area (1). The chemical composition of the pollutant hydrocarbons is determined and the most appropriate combination of microorganisms is selected. The bacterial composition is prepared in a reactor.

The polluted water is extracted from the central well (3) by means of the pump (4) via a special suction nozzle. The hydrocarbons contaminating the extracted water are decomposed in the purification unit (5). The starting concentration of hydrocarbon-degrading bacterial cells is required to be no less than $10^6$–$10^7$ cell/ml of polluted medium. The volume of decontaminant is required to be approximately 1–5% of polluted medium contained in purification unit (5) and the water with the microorganisms which oxidize the hydrocarbons is pumped to the test wells (2).

Closed-circuit car wash installations.

Figure 4:
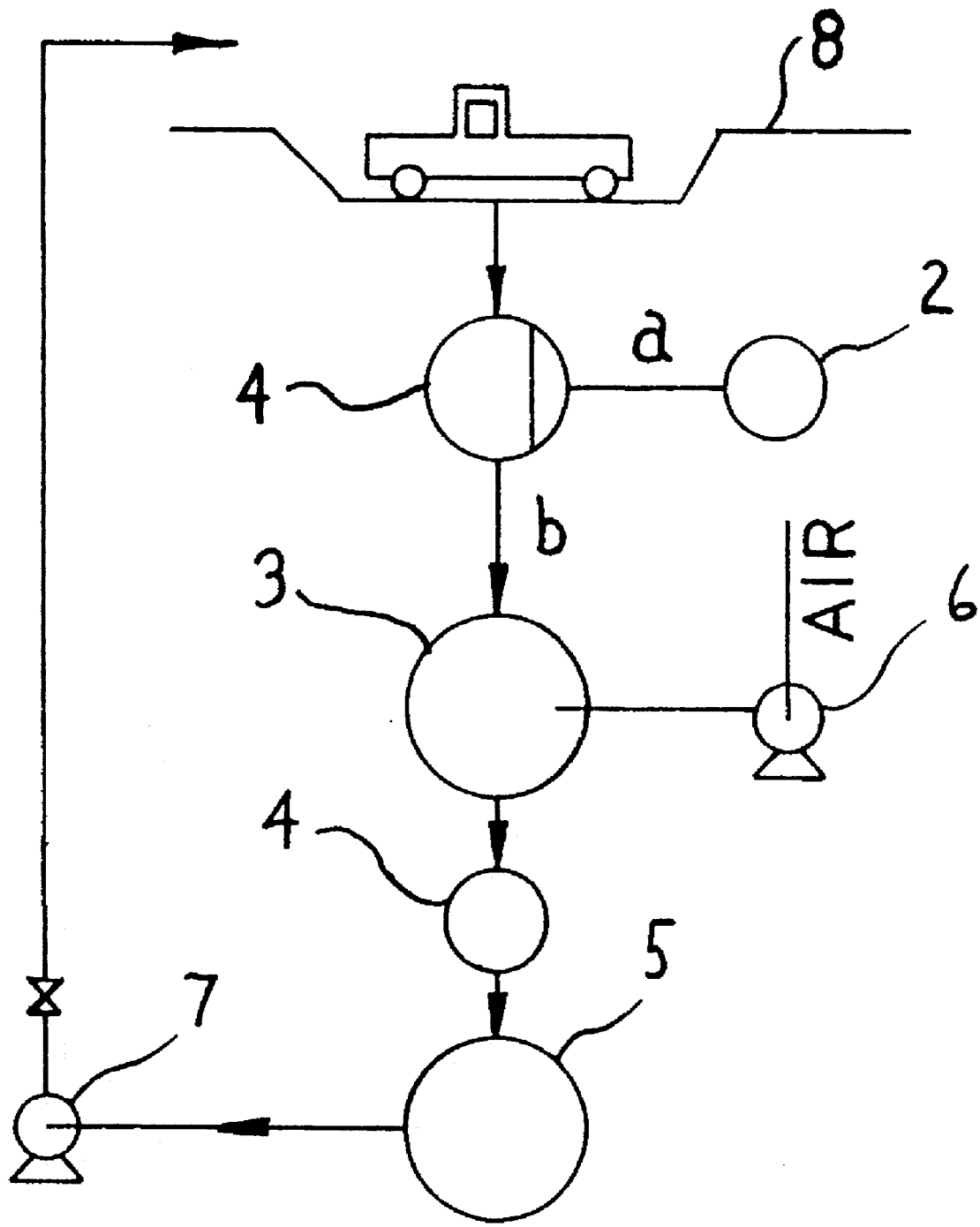
FIG. 4 illustrates a system for treating waste water in a closed-circuit car wash installation using the method of the present invention.

A diagram of a closed-circuit car wash installation is shown in FIG. 4.

The principle of operation is as follows: The car is washed in the installation (8) by jets of water coming from the reservoir (5). The dirty water flows into the water-collection reservoir (1). The reservoir (1) is connected by the pipe (a) the oil-collection reservoir (2), and by the pipe (b) to the bioreactor (3).

The oily pollutants of the collected water are decomposed in the bioreactor (3) by applying the method of the invention. The mixture of the most appropriate bacterial preparation, the inorganic salts and additives is carried to the bioreactor (3), an aeration being carried out for 1–2 hours a day by means of the air compressor (6). The starting concentration of hydrocarbon-degrading bacterial cells is required to be no less than $10^6$–$10^7$ cell/ml of polluted media. The volume of decontaminant is required to be approximately 1–5% of polluted median contained in bioreactor (3).

The purified water travels from the reactor (3) through a sand filter (4) to the reservoir (5), and is used repeatedly for washing cars. If the volume of water decreases owing to evaporation or leakage in the tank (5), more water is added.

The oily pollutants collected in the reservoir (2) are transferred and decomposed in special installations for degradation of oily pollutants.

System for cleaning constantly polluted areas.

Loading/discharge and storage installations are constantly polluted during the work of transporting petroleum crude and petroliferous products in ports and railway stations.

Figure 5:
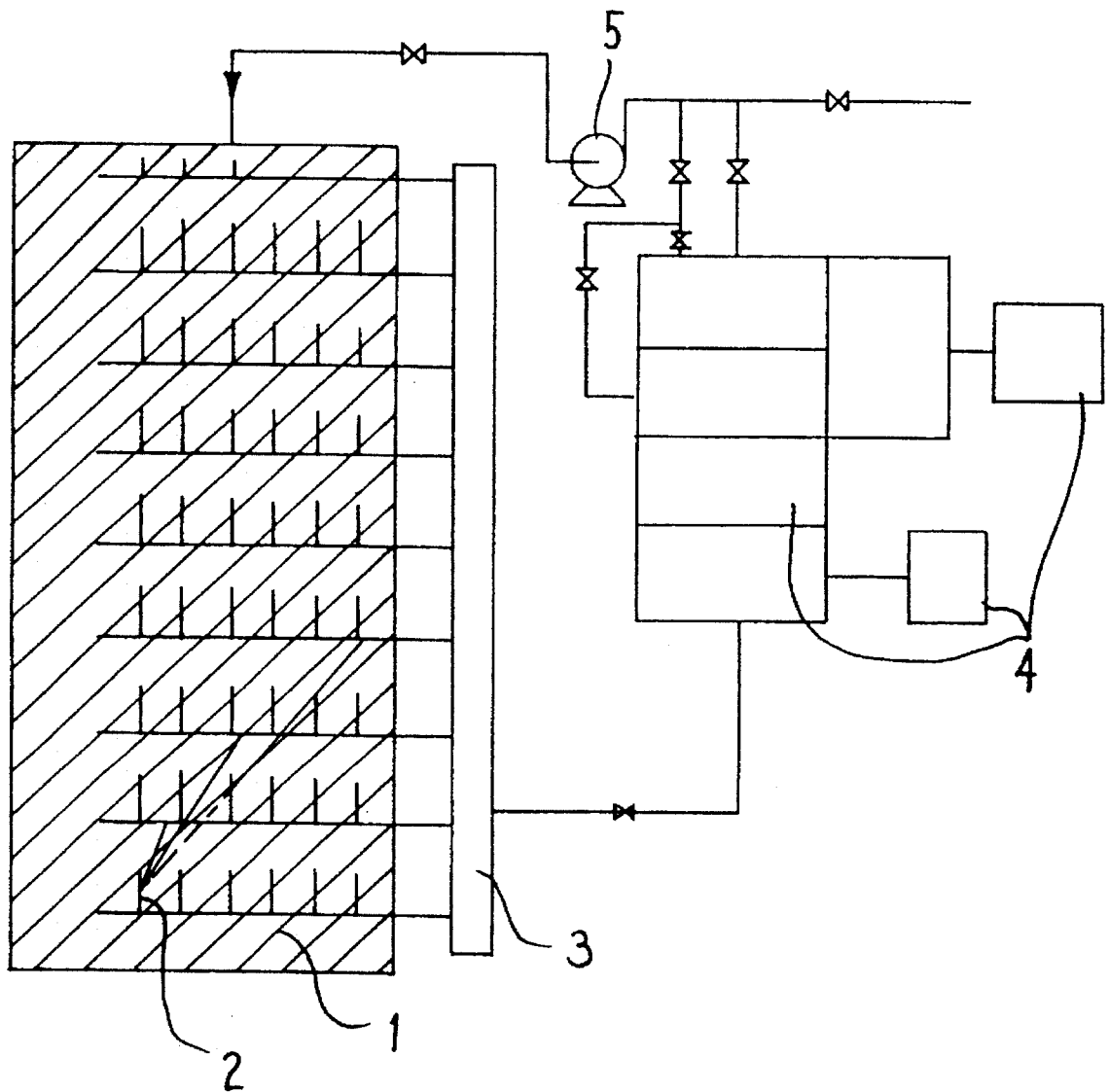
FIG. 5 illustrates a system for cleaning a continuously polluted area using the method of the present invention.

The scheme adopted in these cases is shown in FIG. 5. The petroliferous pollutants accumulated on the surface of the contaminated ground (1) pass through drains (2) to a petroleum collector (3). The petroliferous pollutants collected in the collector, together with rainwater or water used for cleaning the ground, are transferred to the treatment unit (4), where a mechanical and biological purification is carried out as described above in the case of decontamination of waste waters.

The content and quantity of pollutants are determined and, on the basis thereof, the appropriate microorganisms are selected. The preparation of the bacterial composition is checked in one of the checking units (4), in which the bacterial preparation, inorganic salts and necessary additives are mixed. The concentration of hydrocarbon-degrading bacterial cells in the suspension is required to be no less than $10^6$–$10^7$ cells/ml. The volume of decontaminant for one spraying is required to be no less than 1 liter for 1 sq.m. of polluted area. The solution is used in multiple sprayings over the polluted area, according to the quantity and severity of the pollution.

The petroleum crude and the petroliferous products are partially degraded in the installation and are transferred through the drains to the purification unit, where the last part of the degradation takes place. This method of decontamination prevents the spread of petroliferous pollutants into the environment.

Purely by way of illustration, and without any implied limitation attaching to the descriptions below, the following examples are described.

EXAMPLE 1

Owing to a railway accident, petroleum crude was spilled. The polluted area of ground was 20,000 $m^2$. The concentration of pollutant crude was about 3 kg/$m^2$. The total quantity of pollutant was 60 tons. Decontamination was started 20 days after the accident.

Adopting the method proposed in the invention, it was found on analysis that the crude was composed of: 60% of aromatics, 25% of aliphatics and 10% of asphaltenes. According to this composition, and in accordance with Table 3 shown above, the most appropriate microorganisms were selected, a bacterial composition being prepared composed of 1.2 kg of dry preparation of *Azotobacter vinelandii* 21, 0.5 kg of Pseudomonas sp. 19 and 0.3 kg of Pseudomonas sp. 31, suspended in an aqueous solution of inorganic fertilizers which supplied 600 kg of nitrogen and 60 kg of phosphorus, forming a total of about 60 $m^3$ of decontaminating composition having a concentration of $10^6$ cells/ml.

The bacterial composition was sprayed over the contaminated region, in the proportion of 3 liters of bacterial suspension to each $m^2$ of ground. Two months after the treatment, the quantity of pollutant had fallen to 12% of the initial value.

EXAMPLE 2

A natural reservoir of fresh water of surface area about 1000 $m^2$ was polluted with a total quantity of 500 kg of petroliferous products. These had the following composition: 41% of aromatics, 39% of aliphatics and 20% of asphaltenes.

To prepare the decontaminating microbial composition, 51 g of dry preparation of *Azotobacter vinelandii* 21, 49 g of Pseudomonas sp. 9 and 25 g of Pseudomonas sp. 31 were mixed, and the mixture was added to a solution of inorganic salts and additives, forming a total of 2 m$^3$ of suspension, with a bacterial concentration of 2×10$^6$ cells/ml.

The prepared composition was sprayed over the polluted region in the proportion of 2 l/m$^2$. Twenty days after the treatment, no pollutants were to be found in the reservoir.

EXAMPLE 3

This is a similar case to that of Example 2, but on this occasion salt water was involved.

In this case, and according to the information in Table 3, a bacterial composition containing preparations of *Azotobacter vinelandii* 21, Pseudomonas sp.9 and *Acinetobacter calcoaceticus* 23 was used. The results were similar. The prepared suspension with a bacterial concentration of 2×10$^6$ cells/ml was sprayed over the polluted regions in the proportion of 2 l/m$^2$.

The embodiments of the invention in which an exclusive property or privilege is claimed are defined as follows:

1. A method of decontaminating a hydrocarbon-polluted environment, said method comprising the steps of:

analyzing the hydrocarbon pollutants and determining the type and quantity of hydrocarbon pollutants present;

selecting two or more bacterial strains selected from the group consisting of *Azotobacter vinelandii* 21, Pseudomonas sp. 9, Pseudomonas sp. 19, Pseudomonas sp. 31 and *Acinetobacter calcoaceticus* 23 to be used in decomposing said hydrocarbon pollutants, the type and quantity of said bacterial strains to be used being based on the analysis of the hydrocarbon pollutants and the type of environment; and contacting said hydrocarbon-polluted environment with said bacterial strains to effect decomposition of said hydrocarbon pollutants.

2. The method of claim 1, wherein the environment is selected from the group consisting of soil, fresh water, salt water and industrial waste effluents.

3. The method of claim 1, wherein the hydrocarbon pollutants are selected from among anthracene, octadecane, decalin, asphaltenes and mixtures thereof.

4. The method of claim 1, wherein the hydrocarbon pollutants comprise anthracene and the bacterial strains comprise *Azotobacter vinelandii* 21.

5. The method of claim 1, wherein the hydrocarbon pollutants comprise octadecane and the bacterial strains comprise Pseudomonas sp. 9.

6. The method of claim 1, wherein the hydrocarbon pollutants comprise octadecane and the bacterial strains comprise Pseudomonas sp. 19.

7. The method of claim 1, wherein the hydrocarbon pollutants comprise decalin and the bacterial strains comprise Pseudomonas sp. 31.

8. The method of claim 1, wherein the hydrocarbon pollutants comprise asphaltenes and the bacterial strains comprise Pseudomonas sp. 31.

9. The method of claim 1, wherein the hydrocarbon pollutants comprise asphaltenes and the bacterial strains comprise *Acinetobacter calcoaceticus* 23.

10. The method of claim 1, wherein the type of environment is soil and the bacterial strains comprise Pseudomonas sp. 19.

11. The method of claim 1, wherein the type of environment is fresh water and the bacterial strains comprise *Azotobacter vinelandii* 21.

12. The method of claim 1, wherein the type of environment is salt water and the bacterial strains comprise Pseudomonas sp. 9.

13. The method of claim 1, wherein the hydrocarbon pollutants comprise an aromatic compound, the environment is selected from among soil and water and the bacterial strains comprise *Azotobacter vinelandii* 21.

14. The method of claim 1, wherein the hydrocarbon pollutants comprise an aliphatic compound, the environment is water and the bacterial strains comprise Pseudomonas sp. 9.

15. The method of claim 1, wherein the hydrocarbon pollutants comprise an aliphatic compound, the environment is soil and the bacterial strains comprise Pseudomonas sp. 19.

16. The method of claim 1, wherein the hydrocarbon pollutants comprise an asphaltene compound, the environment is selected from among soil and fresh water and the bacterial strains comprise Pseudomonas sp. 31.

17. The method of claim 1, wherein the hydrocarbon pollutants comprise an asphaltene compound, the environment is sea water and the bacterial strains comprise *Acinetobacter calcoaceticus* 23.

* * * * *

UNITED STATES PATENT AND TRADEMARK OFFICE
CERTIFICATE OF CORRECTION

PATENT NO. : 5 494 580
DATED : February 27, 1996
INVENTOR(S) : Egidijus Vladas BASKYS et al It is certified that error appears in the above-indentified patent and that said Letters Patent is hereby corrected as shown below:

In the title page, change "[22] Filed: Mar. 30, 1993" to ---[22] Filed: Sep. 30, 1993---.

Signed and Sealed this

Eighteenth Day of June, 1996

Attest:

BRUCE LEHMAN

Attesting Officer    Commissioner of Patents and Trademarks